United States Patent
Bienhaus et al.

[11] Patent Number: 5,846,489
[45] Date of Patent: Dec. 8, 1998

[54] SYSTEM FOR OPENING CLOSURES OF VESSELS AND FOR THE CONTAMINATION-FREE OPERATION OF REACTION SEQUENCES

[75] Inventors: Gerhard Bienhaus, Wielenbach; Hans Lange, Lampertheim, both of Germany

[73] Assignee: Boehringer Mannheim GmbH, Mannheim, Germany

[21] Appl. No.: 834,043

[22] Filed: Apr. 11, 1997

Related U.S. Application Data

[63] Continuation of Ser. No. 417,865, Apr. 7, 1995, abandoned.

[30] Foreign Application Priority Data

Apr. 9, 1994 [DE] Germany .......................... 44 12 286.1

[51] Int. Cl.$^6$ .............................. G01N 1/00; G01N 35/10
[52] U.S. Cl. .............................. 422/63; 422/99; 422/104; 436/43; 436/174; 436/183; 81/3.07; 81/3.2; 81/3.36; 81/3.4
[58] Field of Search ................................. 422/63, 65, 67, 422/99, 100, 102, 104; 436/43, 47, 48, 49, 51, 54, 174, 180, 807, 809, 810, 183; 81/3.07, 3.2, 3.36, 3.4

[56] References Cited

U.S. PATENT DOCUMENTS

| | | | |
|---|---|---|---|
| 3,005,564 | 10/1961 | Weichselbaum . | |
| 3,991,617 | 11/1976 | Marteau D'Autry | 72/425.4 |
| 4,034,884 | 7/1977 | White . | |
| 4,217,798 | 8/1980 | McCarthy et al. | 81/3.2 |
| 4,312,695 | 1/1982 | Willis | 156/844 |
| 4,876,926 | 10/1989 | Muszak | 81/3.2 |
| 4,960,219 | 10/1990 | Jordan et al. . | |
| 4,982,553 | 1/1991 | Itoh | 53/246 |
| 5,145,646 | 9/1992 | Tyranski . | |
| 5,209,903 | 5/1993 | Kanamori et al. | 422/65 |
| 5,223,227 | 6/1993 | Zuckerman | 422/102 |
| 5,255,574 | 10/1993 | Wuerschum | 81/3.2 |
| 5,282,543 | 2/1994 | Picozza et al. . | |
| 5,340,544 | 8/1994 | Nishikawa et al. | 422/99 |
| 5,443,791 | 8/1995 | Cathcart et al. | 422/65 |
| 5,458,854 | 10/1995 | Burns | 422/102 |
| 5,472,669 | 12/1995 | Miki et al. | 422/63 |
| 5,481,946 | 1/1996 | Nishikawa et al. | 81/3.2 |

FOREIGN PATENT DOCUMENTS

| | | |
|---|---|---|
| A-0 517 092 A1 | 12/1992 | Belgium . |
| 0 65926A1 | 12/1982 | European Pat. Off. . |
| A-0 100 664 A2 | 2/1984 | European Pat. Off. . |
| 0 076772A3 | 5/1984 | European Pat. Off. . |
| A-0 325 763 B1 | 8/1989 | European Pat. Off. . |
| A-0 391 746 A2 | 10/1990 | European Pat. Off. . |
| 0 487492A1 | 5/1992 | European Pat. Off. . |
| A-0 488 769 A2 | 6/1992 | European Pat. Off. . |
| A-0 496 483 A2 | 7/1992 | European Pat. Off. . |
| A-0 517 093 A2 | 12/1992 | European Pat. Off. . |
| A-0 557 828 | 9/1993 | European Pat. Off. . |
| 1407571 | 6/1965 | France . |
| 1424765 | 12/1965 | France . |
| 1452206 | 8/1966 | France . |

(List continued on next page.)

OTHER PUBLICATIONS

DPA–DV–Rolle, Erfindungen und Patente (GE–D), Frau Wedel, Mannheim Dec. 5, 1994; pp. 6–7.

Chemometrics and Intelligent Laboratory Systems, Bd. 17, Nr. 1, Oct. 1992, Amsterdam, pp. 15–45.

*Primary Examiner*—Long V. Le
*Attorney, Agent, or Firm*—Nikaido, Marmelstein, Murray & Oram LLP

[57] ABSTRACT

System for the automatic operation of reactions using several vessels which can be closed by individual closures using a device for automatically opening the closures.

16 Claims, 8 Drawing Sheets

FOREIGN PATENT DOCUMENTS

| | | |
|---|---|---|
| 1275795 | 8/1968 | Germany . |
| 6927506 | 12/1969 | Germany . |
| 88 08 738.7 | 7/1988 | Germany . |
| 42 12 821 C2 | 7/1994 | Germany . |
| 55-93649 | 12/1980 | Japan . |
| 1-132542 | 9/1989 | Japan . |
| 5-38565 | 5/1993 | Japan . |
| 5-232122 | 9/1993 | Japan . |
| 5-288755 | 11/1993 | Japan . |
| 2246081 | 1/1992 | United Kingdom . |
| WO84/02775 | 7/1984 | WIPO . |
| WO92/01814 | 2/1992 | WIPO . |
| WO92/07957 | 5/1992 | WIPO . |

SYSTEM FOR OPENING CLOSURES OF VESSELS AND FOR THE CONTAMINATION-FREE OPERATION OF REACTION SEQUENCES

This application is a continuation of application Ser. No. 08/417,865 filed Apr. 7, 1995.

BACKGROUND OF THE INVENTION

1. Field of the Invention

The invention concerns a system for automatically carrying cut reactions in reaction vessels as well as suitable reaction vessels and closures.

An essential component of health systems is the detection of diseases by means of so-called medical diagnostics. This involves carrying out detection reactions or particular analytes using samples that have been taken from patients who may have been stricken by diseases. Substrates of enzyme reactions, the enzymes themselves, antigens and recently also nucleic acids have proven to be suitable analytes. In this connection the analysis of the latter substances is often made considerably more difficult since the concentrations that are present are occasionally very small. A prerequisite for reliable results is a process that is free from carry-over since the slightest concentrations of interfering substances have a major influence on the measured result. Particularly in the case of tests in which several analyses are carried out successively in one instrument there is a considerable risk of carry-over.

2. Description of the Related Art

In nucleic acid diagnostics the detection limit was considerably reduced by the provision of amplification methods such as for example the polymerase chain reaction (U.S. Pat. No. 4,683,195). However, in return the risk of falsifying the measured results by contaminations is also increased above all by the formation of aerosols in the air. For this reason it was also proposed that the preparation of the samples to be analyzed and the amplification should be carried out in separate rooms. Further suggested solutions are overlayering with oil or wax and the use of an internal enzymatic decontamination system of lower sensitivity (U.S. Pat. No. 5,035,996). However, these solutions are laborious and poorly suited to an automatic operation of several reactions.

In the case of the polymerase chain reaction special tubes are used which, through their conical shape, enable a good heat transfer from a heater located below. In addition most of the instruments used to carry out the thermocycles utilize a cap heater (ca. 100° C.) to reduce evaporation and to avoid condensation.

Plates have also been described which contain several reaction vessels which can be closed by means of a common cover that can be manually torn off. A disadvantage of this design is that when the plate is opened, splashes from one reaction vessel may go into an adjacent one and thus amplify the risk of carry-over.

EP-A-0 408 280 also describes reaction vessels in an open 96-well microtitre plate format. The contamination risk in this case is also very high.

All previously described proposals for vessels for the automatic processing of several reactions have the disadvantage that the reaction vessels can either not be effectively closed or that the reaction vessels have locking caps that are not amenable to automation. These systems can therefore only be used for a routine application of high throughput with a considerable risk of contamination.

SUMMARY OF THE INVENTION

The invention concerns a system for automatically carrying out reactions in reaction vessels comprising:

several reaction vessels, several individual closures for these reaction vessels, a device for automatically opening these closures and an automatic pipetting device.

The above-mentioned technology can be used in the same way to operate sample and reagent storage vessels.

The invention also concerns suitable reaction vessels and closures for such systems.

The system according to the invention is suitable for automatically carrying out reactions. In this connection automatic denotes an operation in which manual operating steps after the sample has been introduced into the system up to the time at which the measured result is obtained are avoided. The operating steps proceed in a predetermined manner in the system preferably separated by a computer program. The system is in addition suitable for carrying out several sequential reactions and even in different reagent storage vessels.

In principle it is possible to perform any type of chemical reaction in the system according to the invention. These include in particular processes in which must be passed through by components of a sample during the course of an analysis. The reactions that occur depend on the type of analyte to be determined. Thus for example immunologically active compounds are usually determined by means of immunological detection methods. In this case interactions between antigens and haptens on the one hand and antibodies that are directed towards them on the other hand are utilized. In the case of nucleic acid tests, the relatively specific interaction between nucleic acids that are essentially complementary to one another is used.

Analytical methods for nucleic acids can be essentially divided into the steps sample preparation, nucleic acid processing and detection of the treated nucleic acids. The system according to the invention is designed particularly for carrying out the nucleic acid treatment reactions. These reactions include in particular the amplification of the nucleic acids. There are a number of methods for this. While there are amplifications that are carried out isothermally such as the method described in EP-A 0 329 822, many other amplifications are carried out using temperature-change cycles (thermocycles) as described for example in EP-A-0 200 362.

The system according to the invention contains several reaction vessels which are suitable for the up-take of reaction liquids. The volume of the reaction liquids is preferably 5 $\mu$l to 5 ml, particularly preferably between 10 $\mu$l and 200 $\mu$l. The reaction vessels are manufactured from a material that is inert towards the reaction solution such as plastics like polystyrene or polypropylene. If it is intended to carry out thermocycles, these reaction vessels must also be thermostable. The PCR tubes from Perkin Elmer that are usually used are for example well-suited as reaction vessels for the present invention.

An essential feature of the present invention is the use of individual closures for these reaction vessels. The individual capping of reaction vessels has previously not been considered and may even have been supported by the fact that designers of plates for tube combinations were obsessed with multiple caps as being particularly suitable. Moreover the use of individual closures is a technical challenge which is accomplished by the individual closures according to the invention. The closures, like the vessels, are preferably manufactured from a preferably thermostable material e.g. polystyrene, polypropylene and particularly preferably by known injection moulding techniques.

Reactions that can be carried cut in the reaction vessel may be of a physical type (e.g. adsorptions) or of a biochemical type (e.g. enzymatic reactions, amplifications etc.).

A further important feature of the system according to the invention is a device for automatically opening the closures. This device is matched technically to the individual closure used in each case.

In order to automatically carry out the reactions, liquids are dispensed into the reaction vessel. The use of an automatic pipetting device, preferably with disposable tips, has proven to be particularly advantageous for this. In this process the components of the reactions to be carried out can be pipetted in any suitable order. It is for example possible to firstly add a sample liquid containing the analyte to the reagent storage vessel. This can if desired be already accomplished outside the system according to the invention and without the automatic pipetting device. In a subsequent step which, if desired, can be carried out using the automatic pipetting device, the reagents required for the reaction are added to the sample liquid in the reaction storage vessel whereby the process according to the invention can also be used.

In another embodiment, the required reagents are previously added in a solid or liquid form to the reaction vessel and the sample liquid is added to this by pipette.

BRIEF DESCRIPTION OF THE DRAWINGS

Reference should be made to the appended drawings on the following description, wherein.

DETAILED DESCRIPTION OF THE PREFERRED EMBODIMENTS

Figure 1:
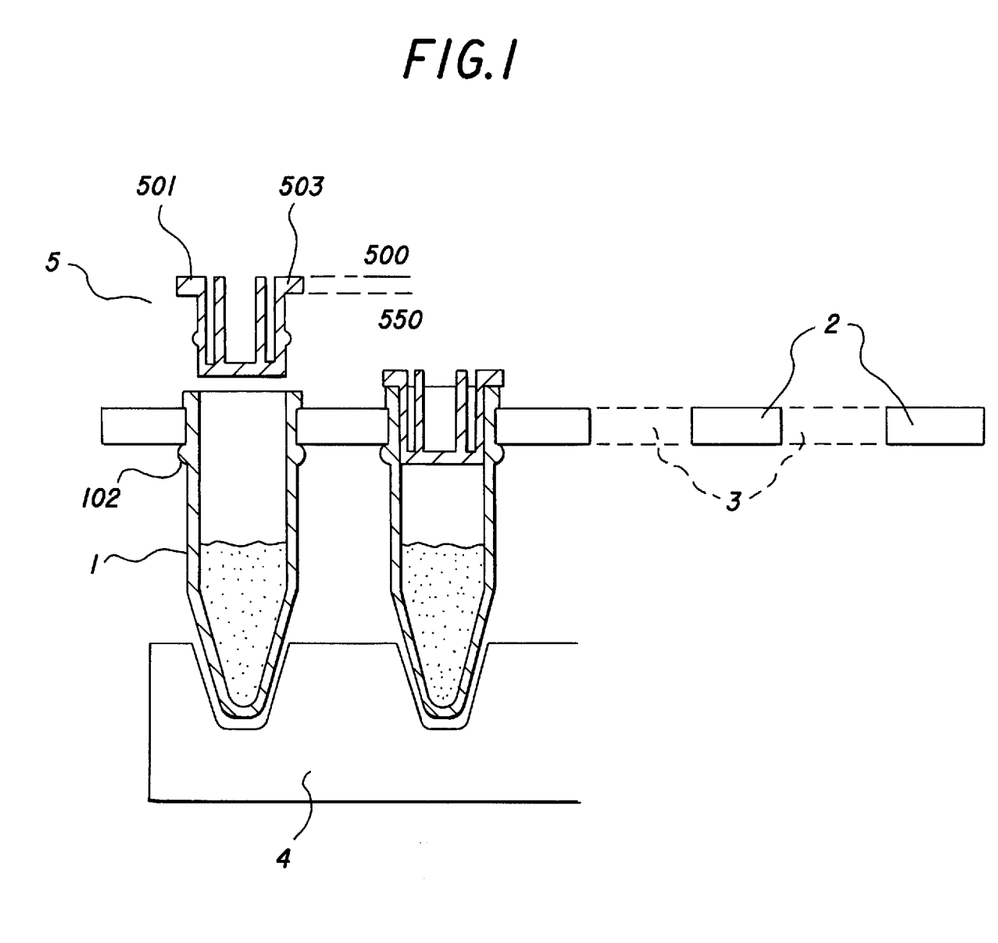
FIG. 1 illustrates a system according to the present invention.

A system for automatically carrying out reactions in a holding plate with 96 wells in a microtritre plate raster is described in the following, this being a particularly preferred embodiment for the arrangement of several reaction vessels. This system is particularly suitable for carrying out the polymerase chain reaction with thermocycling. A holding plate for the Perkin Elmer cycler 9600 instrument is indicated in FIG. 1. A reaction vessel 1 is depicted as being located in one of the holes 3 of a holding plate 2 for 96 tubes. The reaction vessel is fixed in the holding plate by the barb 102. Once the holding plate with the reaction vessels has been inserted into the PCR cycler, the tips of the reaction vessels extend into the thermoblock 4 of the cycler. A cap 5 suitable for the invention is drawn schematically in this Figure. In order to close the reaction vessel, the cap 5 is pressed into the reaction vessel 1 up to a stop 501.

The invention in addition concerns a cap for a reaction vessel which has a part which extends into the opening of the reaction vessel which is characterized in that this part includes a device for removing the cap from the reaction vessel.

The cap according to the invention has at least two parts. One of the parts (reference number 550) is designed in such a way that it extends into the opening of the respective reaction vessel when the reaction vessel is closed by the cap. Another part 500 then still protrudes from the reaction vessel.

The part 550 contains a device 551 for removing the cap from the reaction vessel. In addition this part has a means for sealing the cap against the reaction vessel e.g. sealing lips or sealing rings 552.

The part 500 preferably contains a stop 501 which prevents the cap from completely disappearing into the reaction vessel when this is closed. This also ensures an exact orientation of the cap surface 503. The part 500 of the cap preferably protrudes only very little beyond the opening of the reaction vessel. The parts of the cap protruding from the reaction vessel are essentially flush with the surface 503. This is advantageous when it is intended to use a cap heating to avoid condensation of water vapour from the reaction liquid on the cap. This can then lie flat on the surfaces 503 of several reaction vessels.

All constructional designs which cause the resistance between the device for automatically removing the cap and the cap to become larger than the resistance between the cap and the inner wall of the reaction vessel may be used as the device 551 to remove the cap. Technical design possibilities are for example the use of conical surfaces or rings to engage a device in part 550.

Figure 2:
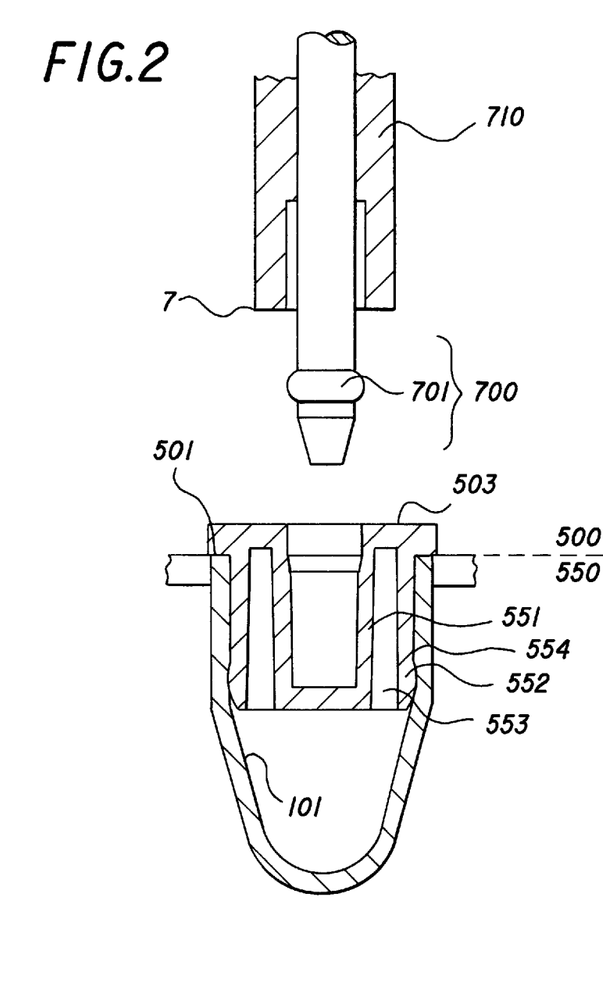
FIG. 2 illustrates a first embodiment of a cap according to the invention, and a removal device.

A first embodiment for a cap according to the invention (in the state of a closed reaction vessel) according to the invention and a suitable opening device 7 are shown in FIG. 2. The devices for removing the cap are designed in this case as a conically shaped recess 551 which is closed to the reaction vessel but is open towards the environment in order to be able to accommodate the tapered removal plug 700 of the device for removing the cap. In this process a component presses against the inner wall 101 of the reaction vessel which has a circular sealing ring 552. A particularly advantageous structural detail of the cap according to the invention is the constructional separation of the device 551 from the sealing lip 552 so that when the tapered removal plug is inserted into the part 550, the pressure exerted on the devices does not lead to a substantial increase in the pressure on the sealing lip. This avoids a strong increase in the tight fit of the cap when the tapered removal plug 700 is inserted. The constructional separation is accomplished in FIG. 2 by providing an intervening space 553 between the devices 551 and the sealing lip 552. In FIG. 2 this intervening space is open to the interior of the reaction vessel. Since the surface 503 of the cap is relatively large in the present case, the contact surface for a cap heater and the heat transfer from the heater to the cap is particularly large.

Figure 3:
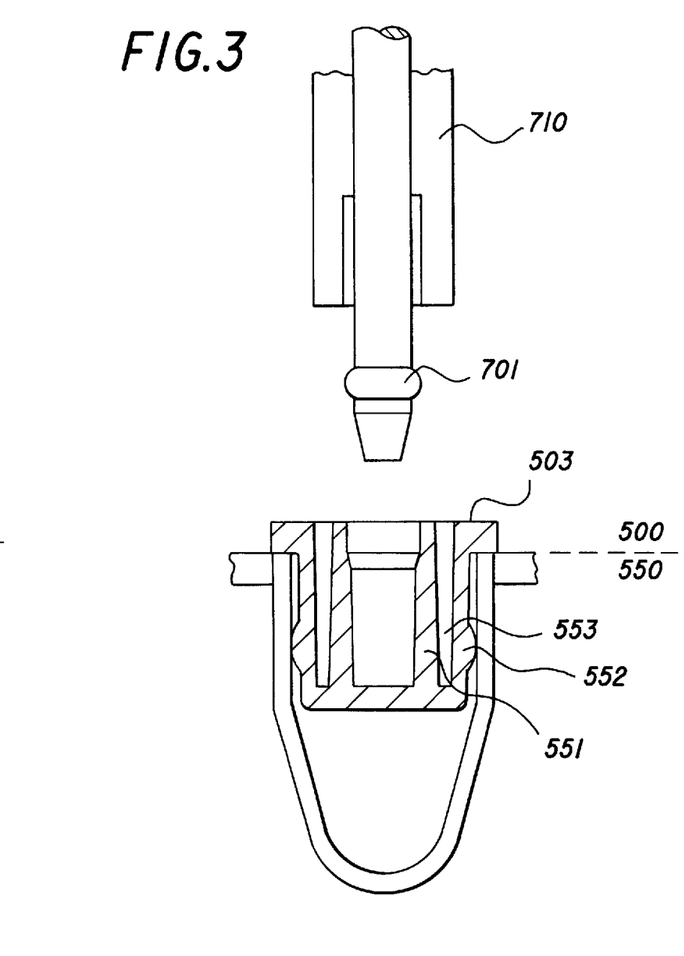
FIG. 3 illustrates a second embodiment of a cap, and a removable device according to the present invention.

A particularly advantageous cap is shown in FIG. 3. The essential difference to the cap shown in FIG. 2 is that the intervening space 553 is designed not to be opened to the reaction vessel but rather to the environment. This embodiment has the advantage that the contact surface of the cap for the reaction solution or the overlying gas space is small so that only a small surface is available for possible condensation of liquid on the cap.

Figure 4:
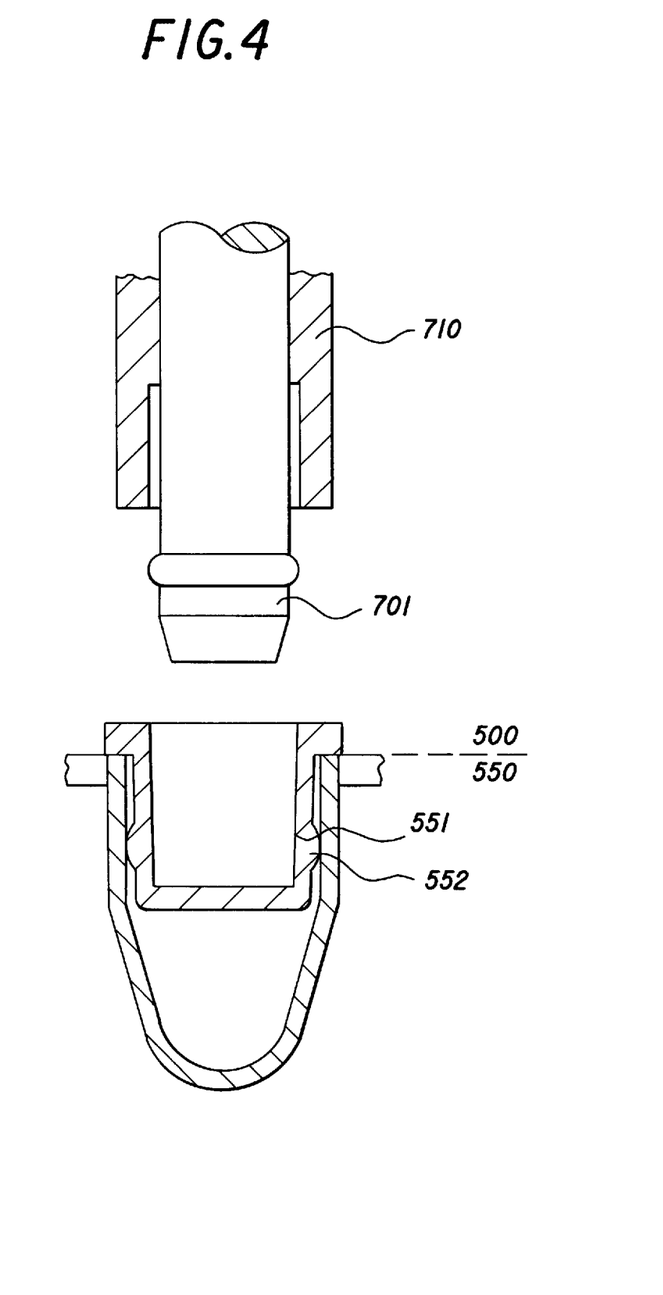
FIG. 4 illustrates a third embodiment of a cap according to the present invention, and a removable device.

A cap is shown in FIG. 4 in which no intervening space 553 is provided. Although this cap can also be used for the system according to the invention, it has the disadvantage that when the tapered removal plug is inserted, the pressure on the inner wall of the reagent storage vessel increases and thus a larger force is required to remove the cap from the reaction vessel than in the cases described above.

The device for automatically opening the closures is matched to the shape of the devices in the cap for removing the cap. Tapered plugs have proven to be particularly advantageous which have a removal ring 701 which has to be pressed into the part 550 over a corresponding resistance of the cap. When the tapered plug is withdrawn the ring acts as a resistance. Since the pressure of the cap on the inner wall of the reaction vessel is smaller than the resistance of the ring with the cap, the cap is removed from the reaction vessel.

In order that the tapered removal plug 7 can be used several times, the device preferably also includes a component for stripping the cap removed from the reaction vessel from the tapered removal plug. This can for example be a stripping jacket 702.

The device is aligned with the arrangement of the reaction vessels for processing samples in reaction vessels. If a composite plate is used, the device is therefore located on a X-Y transport unit with which the device can be moved over the respective reaction vessel. The tip of the tapered removal plug is inserted into the cap by moving the tapered removal plug 700 towards the closed reaction vessels (Z direction). This movement will usually be perpendicular to the transport plane. Although both movement processes can in principle be carried out by any computer-controlled robot, it is also possible to convert conventional automated pipettors, e.g. from Tecan, by replacing the gear rack that is usually used for pipetting by a gear rack with a device 7. It is also possible to attach the device for automatically opening the cap, in addition to the pipetting unit, on a gear rack of an automated pipettor. The automated pipettor is programmed accordingly.

In order to process several reaction vessels concurrently e.g. one row of a microtitre plate, several devices 7 can be mounted on a transport unit so that several individual caps can be opened simultaneously. However, this embodiment would not appear to be preferable with regard to avoiding contaminations.

The present invention, in particular the automatically operable cap, cannot only be used for reaction vessels but for all types of vessels in a system for carrying out several reactions. These also include, in addition to vessels in which a reaction between several reaction partners proceeds and which are referred to as reaction vessels in this case, vessels in which the individual reaction partners for the desired reaction are stored. In the case of the analysis of liquid samples it is possible to distinguish between sample vessels and reagent storage vessels. A liquid is stored in a sample vessel which it is intended to examine for the presence or the amount of one or several analytes. After sample collection (e.g. collection of blood of a patient who is to be examined) and possible processing (isolation of plasma or serum), the sample liquid is transferred into a sample vessel and, if desired, is closed with an automatically operable cap according to the invention. Then the sample vessel is inserted individually or together with further sample vessels into the system e.g. an automated analyzer. In order that a process according to the invention may proceed, the cap is removed from the sample vessel and the desired amount of sample liquid is removed before carrying out the transfer of sample liquid from the sample vessel into a reaction vessel. An advantage of the system according to the invention, in which the sample vessels are also closed by means of an automatically operable cap, is that the sample vessel can be easily closed again by means of the same cap or of a new cap. In the preferred case of recapping with a new cap, the old cap is transferred from the tapered removal plug by the stripping jacket into a waste vessel and a new cap is drawn onto the tapered removal plug from a storage vessel for caps. The new cap is then placed on the sample vessel and the tapered removal plug is removed, the cap remaining on the sample vessel. The cap is removed again for a further determination of a further analyte from the same sample and in turn a certain amount of sample liquid is removed. If the cap has a septum, it is also possible to remove sample from the sample vessel using a piercing pipette without removing the cap.

When reactions are carried out it may be necessary to transfer further reagents into the reaction vessel.

These are stored in reagent storage vessels which may also be closed and opened according to the invention. A reagent storage vessel is therefore understood to mean a storage vessel for reagents, these reagents being used for carrying out reactions in reaction vessels. Since the reagents usually have to be provided in large amounts e.g. for carrying out several reactions, these reagent storage vessels are often in the form of bottles with volumes between 20 and 500 ml. Such reagent storage vessels may also be closed by automatically operable caps according to the invention. This is usually done by the manufacturer. The customer places the reagent storage vessel in a suitable position in the system. As soon as it is intended to carry out a reaction in a reaction vessel which requires the use of the reagent stored in the particular reagent storage vessel, the automatically operable cap is removed from the reagent storage vessel and the required amount of reagent is withdrawn and transferred into the reaction vessel. Subsequently the reagent storage vessel can be closed again by the removed cap or by a new cap (see sample vessel).

In the case of large-volume reagent storage vessels, it is in principle possible to also use the previously used reagent storage vessels when the usual screw caps are modified by the use of the automatically operable cap according to the invention. For this a small opening is preferably provided in the upper side of the screw cap which is then closed with a cap according to the invention. An advantage of this system is that the reagent storage vessel can be filled through a relatively large opening that is closed by the screw cap but, however, the removal of reagent liquid can be carried out through the relatively small opening closed according to the invention.

The invention in addition concerns a process for automatically carrying out chemical reactions in reaction vessels characterized by the steps:

Provision of reaction mixtures in reagent and/or reaction vessels closing the reaction vessels by individual closures and automatically opening the individual closures by means of a device for removing the cap from the vessels.

The process in principle proceeds similarly to the previously known manual processes except that an automatically operable cap is used and it takes place in a system. Of course the automatically operable caps can also be opened and closed manually. A central feature is the provision of reaction vessels which contain a reaction mixture and which are closed by means of an automatically operable cap. This applies particularly to reactions which proceed in thermocycles. After completion of the reaction the cap is detached from the reaction vessel with the aid of a device for removing the cap. This is achieved by insertion of the device into the means provided in the cap and pulling out the device together with the cap. The cap can subsequently be stripped from the tapered removal plug by pulling back the tapered removal plug in a stripping jacket. Afterwards the reaction mixture can be removed from the reaction vessel or processed further therein and if desired, even closed again by means of a (new) cap.

An advantage of the cap according to the invention is the ability to use a cap heater due to the particularly simple possibility of providing it with a flat surface. The transfer of the means for opening the cap into the space below the vessel saves material and enables a compact method of construction. A further advantage is the possibility of keeping the gas space above the reaction solution as small as possible by the parts of the cap that protrude into the reaction vessel. A consequence of this advantage is that the height of the walls of the reaction vessel does not have to be reduced which would be a disadvantage with regard to the potential for splashing during pipetting operations. The amenability of the cap according to the invention to automation facilitates the complete automatability of systems for the detection of analytes in liquids.

The invention can be used in particular for the analysis of components of body fluids according to the principle of immunoassays or nucleic acid diagnostics. Due to the aforementioned advantages, the application for the detection of nucleic acids is particularly preferred. Detection methods for nucleic acids can include steps for carrying out the amplification of nucleic acids in a liquid e.g. like the polymerase chain reaction (EP-B-0 200 362) or another system. Subsequent hybridization reactions with detection probes can also be carried out in the reaction vessels according to the invention. In this case it is also possible to open the reaction vessels several times with the aid of the cap according to the invention.

FIG. 1 shows a composite plate with reaction vessel 1, thermoblock 4 and cap according to the invention.

FIGS. 2 to 4 show caps for carrying out the process according to the invention in an overall view with a suitable removal device and reaction vessel.

Figure 5:
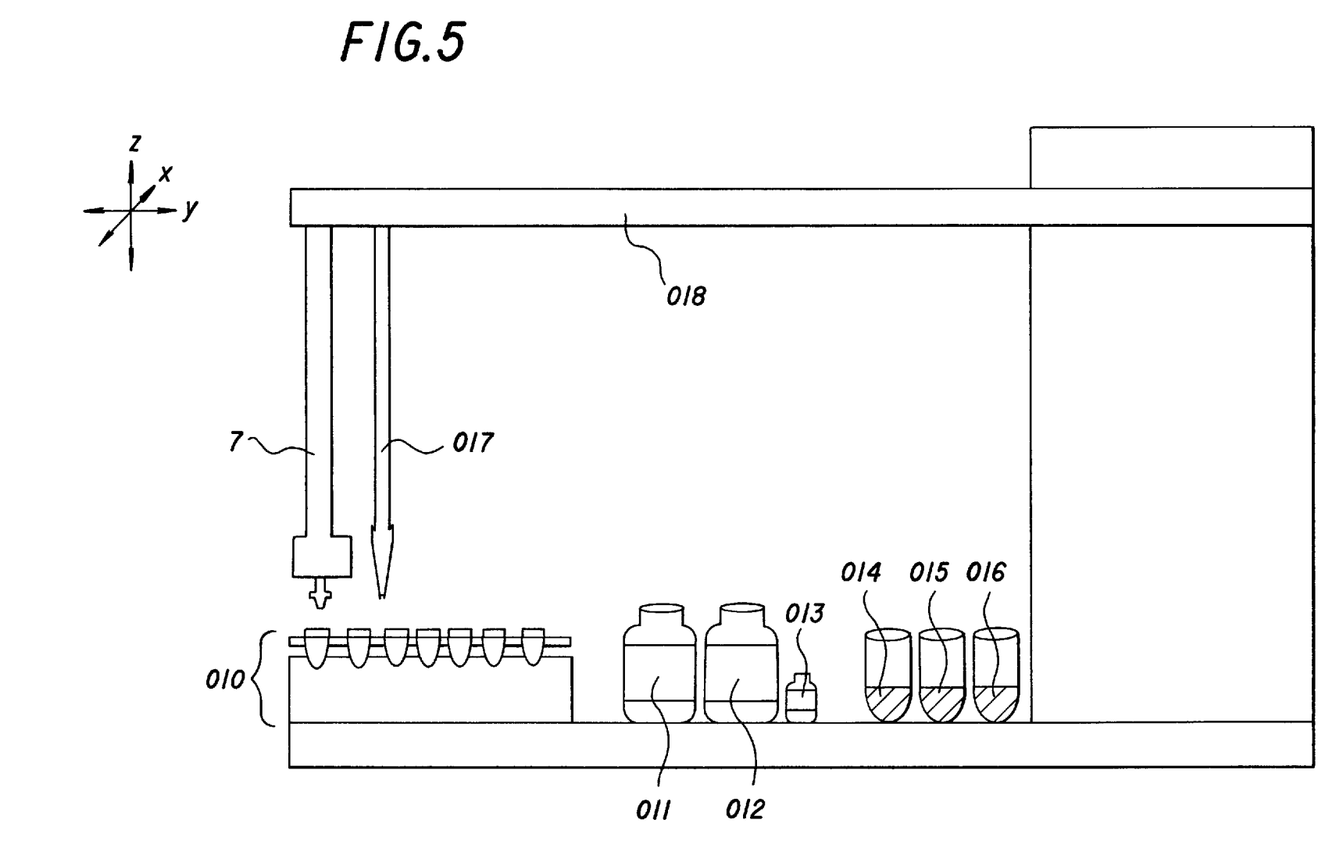
FIG. 5 illustrates another embodiment of a system according to the present invention.

FIG. 5 shows a system according to the invention for carrying out reactions. In this case a composite plate with reaction vessels and caps is indicated by the reference number 010. Reagent storage vessels 011, 012 and 013 and several primary sample vessels 014, 015 and 016 may be provided from which the amounts required for the reaction are withdrawn by the pipetting unit 017 and pipetted into the reaction vessels 5. After closing the reaction vessels, which can if desired, be carried out with the removal device 7, reaction and opening of the cap with the removal device, further reagents can be added by pipette. Then if desired, a measurement of signals is carried out either in the reaction vessel itself or, after removing the reaction mixture, in a measuring unit. The gear rack 018 of the XYZ transport unit of a conventional automated pipettor (e.g. from the Tecan company) is indicated in the Figure.

Figure 6:
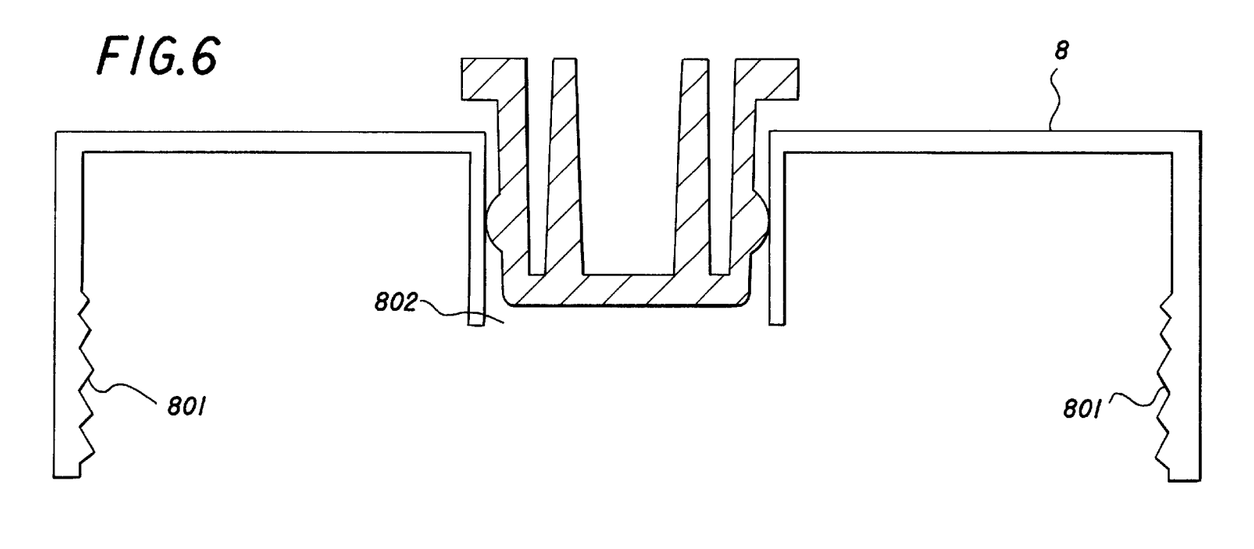
FIGS. 6 and 7 illustrate another embodiment of a cap according the present invention.

The aforementioned risk of contamination can also refer to reagents which stand open on an instrument. FIG. 6 shows an embodiment of a screw cap according to the invention which can be processed with conventional production machines and can subsequently be used in a system. The screw cap 8 has a screw thread 801 and an opening 802 for sampling which can be closed or opened with the aid of a cap according to the invention.

Figure 7:
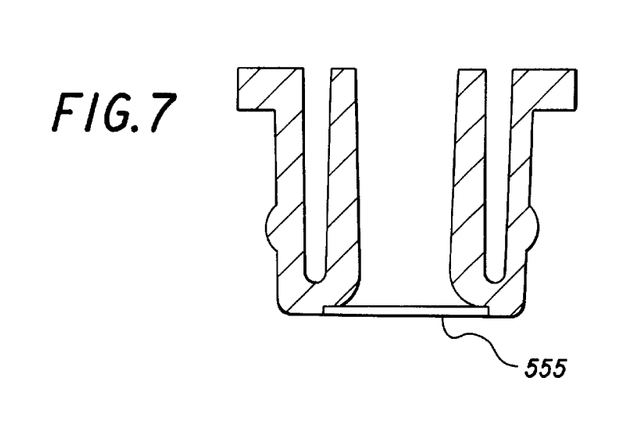

The same applies to samples which, in one embodiment with a septum, can be transferred by a syringe into a special sample tube immediately after blood collection. FIG. 7 shows a modified cap according to the invention for this. It has a septum 555 which can be pierced with a common pipetting needle. The advantage of this embodiment is the possibility of a multiple sample withdrawal without having to remove the cap according to the invention. The septum is preferably located in the part of the cap which extends into the sample vessel.

Figure 8:
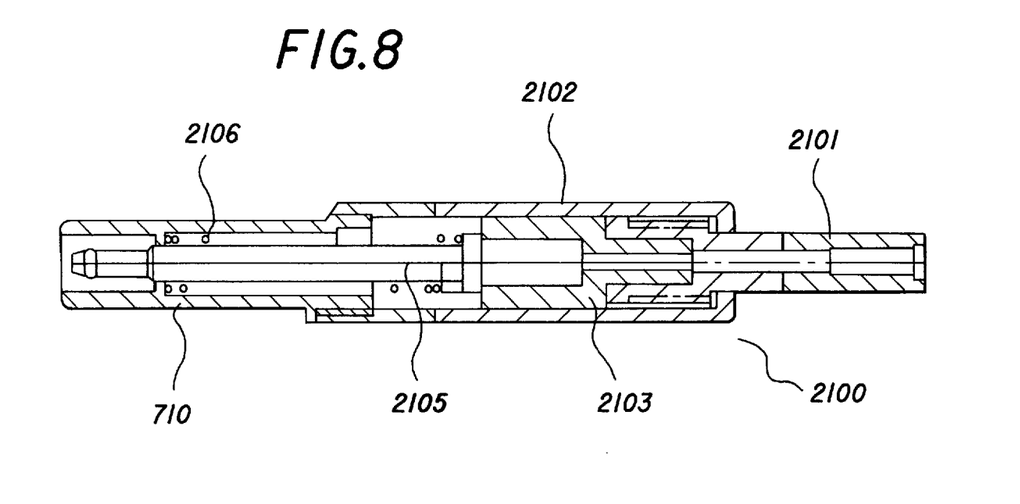
FIGS. 8 and 9 illustrate a removal device according to the present invention.

FIG. 8 shows a stop unit for a removal device. This is operated by means of a pressure piece 2101 which together with the stop element 2103 is held in a starting position by a pressure spring 2106 around a pressure pin 2105. The step element 2103 moves in a stop jacket 2102 and the pressure pin 2105 moves in a release casing 2104.

Figure 9:
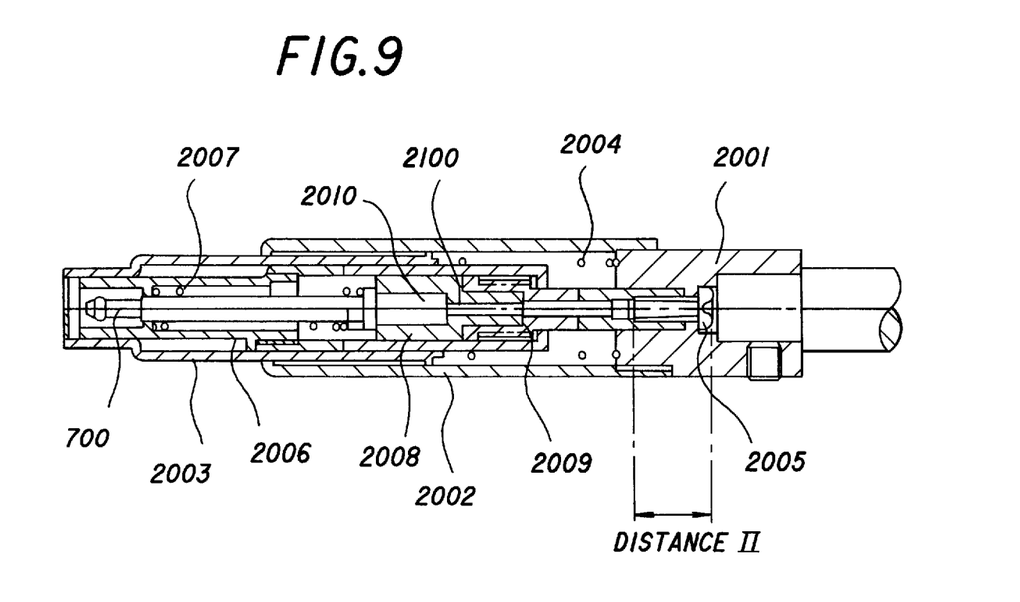

This stop unit can be used manually as well as within a system for removing caps. The stop element is preferably held in an outer casing 2002 which is shown in FIG. 9. The stop unit is marked with the reference number 2100.

Figure 10:
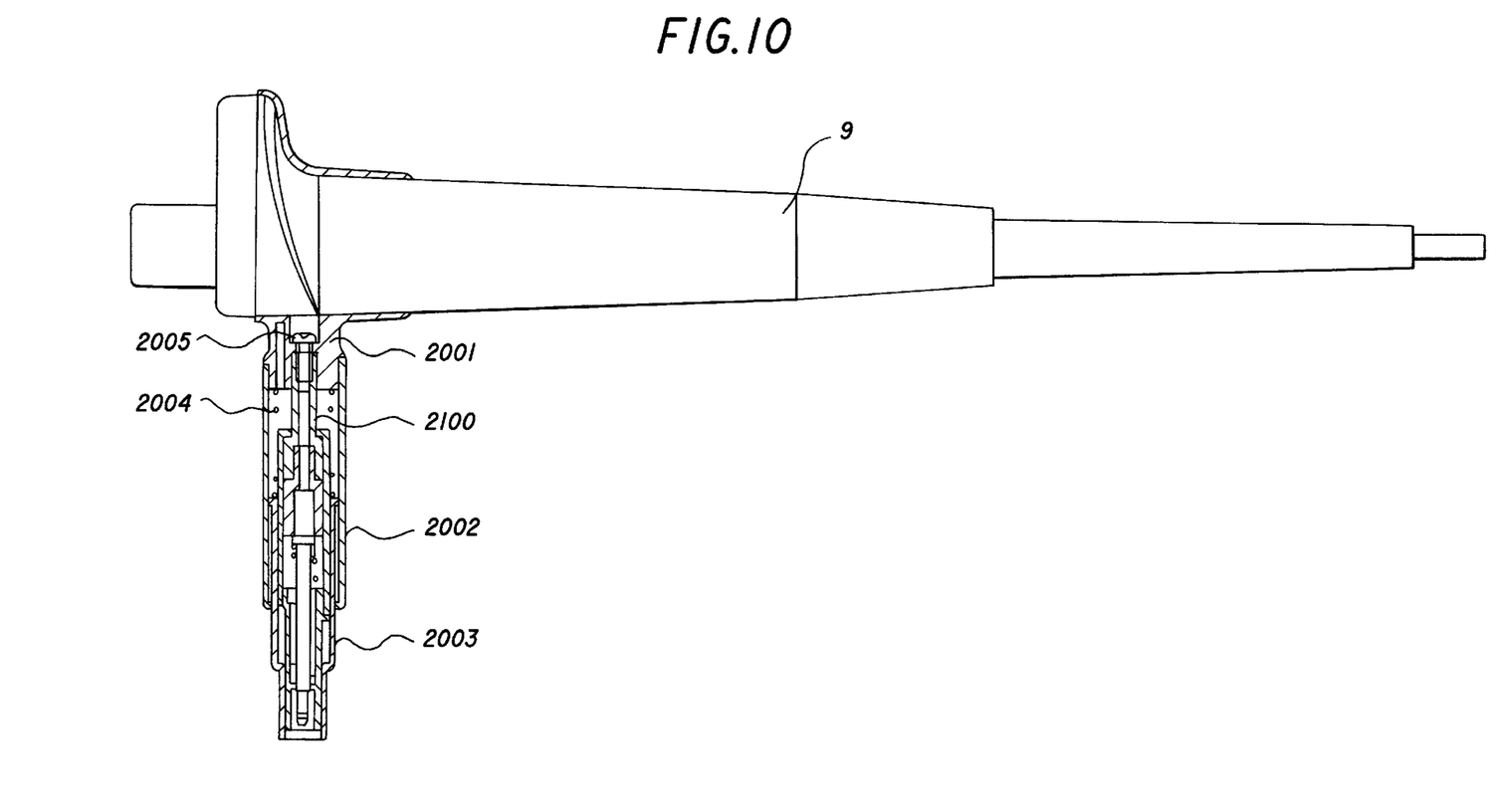
FIG. 10 illustrates another embodiment of a manual removal device.
Figure 11A:
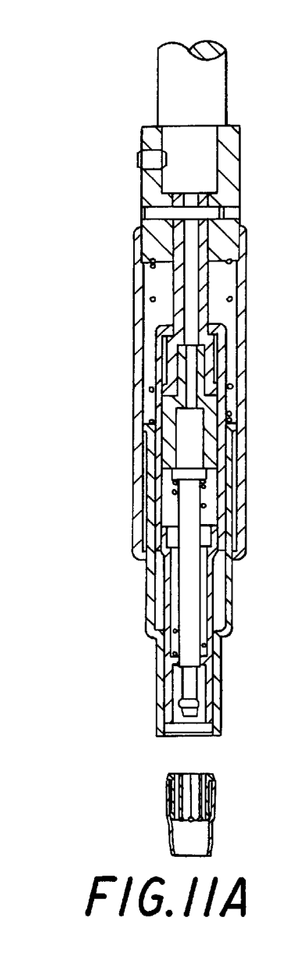
FIGS. 11A–F illustrate the steps for removing a cap from a vessel using a removal device according to the invention.
Figure 11B:
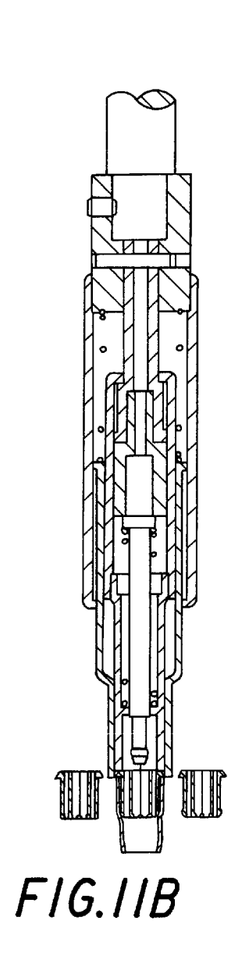
Figure 11C:
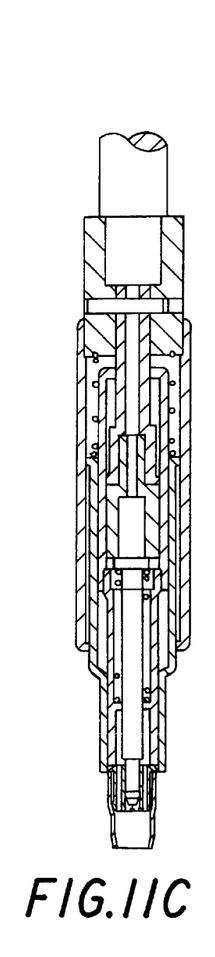
Figure 11D:
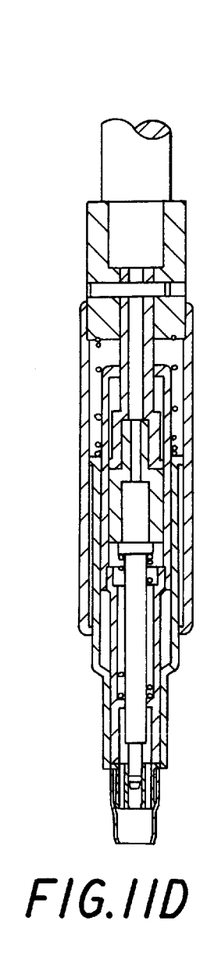
Figure 11E:
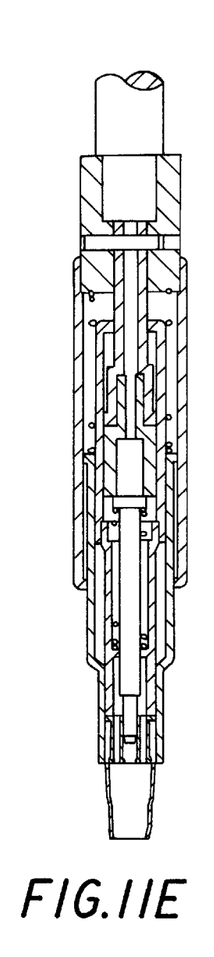
Figure 11F:
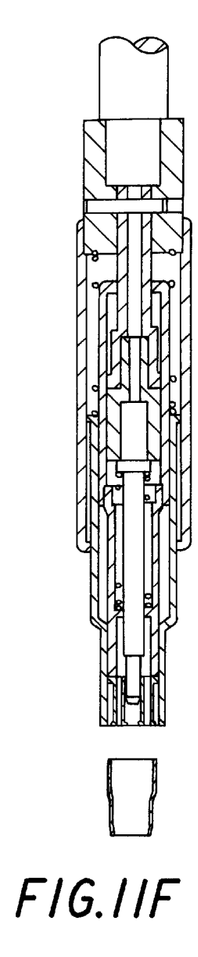

A manual removal instrument is shown in FIG. 10. It contains one sub-assembly in the form of a device to remove or attach the cap and another sub-assembly in the form of a device for pipetting a liquid.

FIG. 11 shows steps A to F for removing a cap from a vessel. Step A shows the initial position of the removal component and a vessel closed by means of a cap according to the invention. In step B the removal element is placed on the component which contains the vessel. In step C the tapered removal plug is inserted into part 550 of the cap. By pulling back the tapered removal plug by a short path length, the tapered removal plug engages at the provided narrow position (step D). The cap is removed from the vessel (step E) by further pulling back the tapered removal plug together with the stripping jacket. The removal unit is lifted from the component with the reaction vessel in step F. In a further step G which is not shown the cap is stripped off by pushing the stripping jacket over the removal ring. Subsequently the removal unit again stands in the initial position or can be transferred back to the initial position (step A).

Another object of the invention is to provide an apparatus for processing a liquid present in a sealed or sealable vessel, with the apparatus containing a pipetting device for the liquid and a device for removing and/or mounting a closure from and to the vessel. The pipetting device for the liquid may be on one hand a commercial piston pipet (for instance made by Eppendorff, BRD). A cap handler or removal unit is mounted to the pipet preferably in the vicinity of the grip. The removal unit preferably operates by the total apparatus applying a pressure to a closed vessel when the cap shall be removed, or by pressure on a non-closed vessel when this vessel shall be closed by a closure means. The caps of the invention were found to be especially appropriate.

When processing the liquids automatically, the removal unit may be mounted to an x, y, z arm of a robot (Tecan (tm)) or of a cylindrically affixed robot arm (for instance by Zymark (tm)). Moreover the cap handler may be used manifold, for instance 8-fold or 12-fold in mutually adjoining positions. The cap handler furthermore may be affixed in another embodiment mode to an arm of a conventional microtitration plate washer (also carrying out x, y, z displacements). Again the removal unit of the invention may be affixed by a thermocycler carrying out thermocyclic reactions such as polymerase chain reactions, so that the cap can be removed in a coordinated manner from vessels receiving reagents. Moreover, the removal unit of the invention may be combined with magnet separators, heaters, or water baths. All such devices are useful when processing liquids.

Consequently, another object of the invention is to provide an apparatus with which to seize a vessel cap, the apparatus containing a tapered removal plug 700 entering the cap inside, such that it clamps in place, and a stripping jacket 710 whereby the seized cap can be stripped from the tapered removal plug or the component which is clamped to the cap. Preferably, the apparatus includes a detent mechanism which for instance may be in the form of a "ballpoint pen" type removal mechanism and which solely by pressure being applied to the apparatus can move along a predetermined sequence of detent positions. Application of the pressure on the outer apparatus shell is especially preferred.

EXAMPLE 1

An operation sequence of an amplification reaction is used in the following as an example of a possible protocol for the interplay between a laboratory robot and the objects of the invention. The interplay of all elements enables the reaction sequence to be carried out automatically.

The prior steps for collecting the sample containing analyte from endogenous liquids (e.g. blood) are carried out according to conventional procedures and are therefore not described. Therefore an analyte in a sample liquid (in this case purified nucleic acid from a blood sample) which is present in a reaction vessel with an individual closure according to the invention is the starting point at the beginning of the sequence of the automatic amplification process.

The system for the contamination-free operation of reaction sequences in addition contains:

a laboratory robot from the Tecan Company (Type RSP9652SLD) arm 1 contains the automatic pipetting unit (017) arm 2 contains the opening and removal device (7), a thermocycler from the Perkin Elmer Company with a composite plate (2) with reaction vessels (1) including individual closures (5), the composite plate is composed of a holding plate with recesses for holding the reaction vessels and a thermoblock (4) which is located below and also has corresponding recesses.

The required reagent vessels, the closed sample with the analyte for the amplification reaction, the measuring cells and the storage vessels, waste containers and pipette tip holder with pipettes are located on the laboratory robot platform. All vessels are closed with individual closures and are opened before use.

The following operation sequence assumes that all units, vessels, elements and substances are ready for operation and that a new start of an amplification reaction is due to begin. The "stand-by" position of the arm denotes a defined position on the laboratory robot platform which is outside the vessel zone and allows the other arm to have a further access to the same vessel. Each of the two arms has its own "stand-by" position.

Operation sequence

| Step | Actions |
|---|---|
|  | Start of the operation sequence |
| 1 | Arm 1 with a pipetting unit moves from its starting position to the pipette tip holder and equips the unit with a new pipette tip, |
| 2 | Arm 2 with an opening and removal device (7) moves from the starting position to the sample vessel containing the analyte (014), |
| 3 | Operating sequence of the opening and removal device (arm 2), device moves into the starting position, the removal element is placed on the cap surface, the tapered removal plug (700) is inserted into the inside of the cap, the tapered removal plug is pressed in by lifting the removal device (7), the cap is removed from the vessel arm 2 with the cap moves from the area of the reaction vessel opening into a "stand-by" position next to the vessel. |
| 4 | Arm 1 with a pipetting unit and pipette tip moves from the pipette tip holder to the sample vessel of the analyte, |
| 5 | Operation sequence for sample withdrawal (arm 1) Lowering the pipetting unit with pipette tip, aspirating the sample liquid into the tip, lifting the pipetting unit with pipette tip plus sample liquid, |
| 6 | arm 1 with the pipetting unit with pipette tip plus sample liquid moves into a "stand-by" position next to the opening of the amplification vessel |
| 7 | arm 2 with cap moves to the opening of the sample vessel containing analyte |
| 8 | Operation sequence for capping and closing (arm 2) Arm 2 with the cap moves over the vessel opening, the cap is lowered onto the vessel, the cap is pulled off from the tapered withdrawal plug of the opening device, the vessel is closed with the cap arm 2 moves to the "stand-by" position. |
| 9 | Arm 2 with the opening and removal device moves from the "stand-by" position to the reaction vessel (1) (amplification vessel) in a defined position on the composite plate. |
| 10 | Operation sequence of the opening and removal device (arm 2) Device (7) moves into the starting position, the withdrawal element is placed on the cap surface of a reaction vessel (1), the tapered withdrawal plug is inserted into the inside of the cap, the tapered withdrawal plug is pressed in, the cap is removed from the vessel, the opening and removal unit with the cap is removed from the vessel, arm 2 with the cap moves from the area of the vessel opening into a "stand-by" position next to the vessel. |
| 11 | Arm 1 with the pipetting unit with pipette tip plus sample liquid moves from the "stand-by" position to the opening of reaction vessel (1) (amplification vessel) |
| 12 | Sample delivery sequence (arm 1) Lowering of the pipetting unit with pipette tip plus sample, the sample liquid is emptied from the tip, the pipetting unit with pipette tip are |

| Step | Actions |
|---|---|
| | lifted off, |
| | arm 1 moves to the waste container, |
| | the used tip is discharged, |
| | arm 1 moves into the starting position. |
| 13 | Arm 2 with the cap moves to the opening of the amplification vessel |
| 14 | Operation sequence for capping and closing (arm 2) |
| | Arm 2 with the cap moves over the vessel opening, |
| | the cap is lowered onto the vessel, |
| | the cap is pulled off from the tapered withdrawal plug of the opening device, |
| | the vessel is closed with the cap arm 2 moves to the "stand-by" position. |
| 15 | Arm 1 with pipetting unit moves from the starting position to the pipette tip holder and equips the unit with a new pipette tip. |
| 16 | Arm 2 with the opening and removal device moves from the "stand-by" position to the reagent vessel on the platform. |
| 17 | Operation sequence of the opening and removal device (arm 2) |
| | Device (7) moves into the starting position, |
| | the withdrawal element is placed on the cap surface the tapered withdrawal plug is led onto the cap surface, |
| | the tapered withdrawal plug is inserted into the inside of the cap, |
| | the tapered withdrawal plug is pressed in, |
| | the cap is removed from the vessel, |
| | the opening and removal unit with the cap is removed from the vessel, |
| | arm 2 with the cap moves from the area of the vessel opening into a "stand-by" position next to the vessel. |
| 18 | Arm 1 with pipetting unit and pipette tip moves from the pipette tip holder to the reagent vessel (011) on the platform. |
| 19 | Reagent withdrawal sequence (arm 1) |
| | Lowering the pipetting unit with pipette tip (if necessary the septum is pierced), |
| | the required amount of liquid is aspirated into the tip, |
| | the pipetting unit with pipette tip plus liquid is lifted off. |
| 20 | Arm 1 with pipetting unit with pipette tip plus liquid moves into the "stand-by" position next to the opening of the amplification vessel. |
| 21 | Arm 2 with cap moves to the opening of the reagent vessel |
| 22 | Operation sequence for capping and closing (arm 2) |
| | Arm 2 with the cap moves over the vessel opening, |
| | the cap is lowered onto the vessel, |
| | the cap pulled off from the tapered withdrawal plug of the opening device using the stripping jacket (710), |
| | the vessel is closed with the cap arm 2 moves to the "stand-by" position. |
| 23 | Arm 2 with opening and withdrawal device moves from the "stand-by" position to the amplification vessel in a defined position on the composite plate, |
| 24 | Operation sequence of the opening and removal device (arm 2) |
| | Device moves into the starting position, |
| | the withdrawal element is placed on the cap surface, |
| | the tapered withdrawal plug is inserted into the inside of the cap, |
| | the tapered withdrawal plug is pressed in, |
| | the cap is removed from the vessel, |
| | the opening and removal unit with the cap is removed from the vessel, |
| | arm 2 with the cap moves from the area of the vessel opening into a "stand-by" position next to the vessel. |
| 25 | Arm 2 with pipetting unit with pipette tip plus liquid moves from the "stand-by" position to the opening of the amplification vessel. |
| 26 | Reagent delivery sequence (arm 1) |
| | Lowering of the pipetting unit with pipette tip plus sample, |
| | the reagent liquid is emptied from the tip, |
| | the pipetting unit with pipette tip is raised, |
| | arm 1 moves to the waste container, |
| | the used tip is discharged, |
| | arm 1 moves into the starting point. |
| 27 | Arm 2 with the cap moves to the opening of the amplification vessel |
| 28 | Operation sequence for capping and closing (arm 2) |
| | Arm 2 with a cap moves over the vessel opening, |
| | the cap is lowered onto the vessel, |
| | the cap is pulled off from the tapered withdrawal plug of the opening device using the stripping jacket, |
| | the vessel is closed with the cap arm 2 moves into the "stand-by" position. |

Steps 15 to 28 represent a cycle which has to be carried each new addition of reagents into the amplification vessel.

If 3 cycles of reagent addition are required as for the commerical kit from the Hoffmann-La Roche Company (PCR buffer, Taq-polymerase, primer), then a further 28 steps have to be carried out.

| Step | Actions |
|---|---|
| 68 | Arm 2 with pipetting unit moves into the starting position |
| 69 | The amplification solution in the vessel runs through a temperature program as recommended in the aforementioned kit or thermocycler |
| 70 | End |
| 71 | Arm 2 with opening and withdrawal device moves from the starting position to the amplification vessel in a defined position on the composite plate |
| 72 | Operation sequence of the opening and removal device (arm 2) |
| | Device moves into the starting position, |
| | the withdrawal element is placed on the cap surface the tapered withdrawal plug is inserted into the inside of the cap, |
| | the tapered withdrawal plug is pressed in, |
| | the cap is removed from the vessel, |
| | the opening and removal unit with the cap is removed from the vessel, |
| | arm 2 with the cap moves from the area of the vessel opening into a "stand-by" position next to the vessel. |
| 73 | Arm 2 with pipetting unit with pipette tip moves from the starting position to the opening of the amplification vessel. |
| 74 | Amplification mixture (arm 1) |
| | Lowering the pipetting unit with pipette tip, |
| | the required amount of liquid is aspirated into the tip, |
| | the pipetting unit with pipette tip plus liquid is raised. |

| | -continued |
|---|---|
| 75 | Arm 1 with pipetting unit with pipette tip plus liquid moves to the "stand-by" position next to the opening of the amplification vessel. |
| 76 | Arm 2 with cap moves to the amplification opening. |
| 77 | Operation sequence for capping and closing (arm 2) Arm 2 with cap moves over the vessel opening, the cap is lowered onto the vessel, the cap is pulled off from the tapered withdrawal plug of the opening device, the vessel is closed with the cap arm 2 moves to the "stand-by" position. |
| 78 | Arm 2 with opening and withdrawal device moves from the "stand-by" position to the measuring cell or to a storage vessel in a defined position on the platform. |
| 79 | Operation sequence of the opening and removal device (arm 2) Device moves into the starting position, the withdrawal element is placed on the cap surface of the measuring cell or the storage vessel, the tapered withdrawal plug is inserted into the inside of the cap, the tapered withdrawal plug is pressed in, the cap is removed from the vessel, the opening and removal unit with the cap is removed from the vessel, arm 2 with the cap moves from the area of the vessel opening into a "stand-by" position next to the vessel. |
| 80 | Arm 2 with pipetting unit with pipette tip plus sample liquid moves from the "stand-by" position to the measuring cell or to the opening of the storage vessel. |
| 81 | Sample delivery sequence (arm 1) Lowering of the pipetting unit with pipette tip plus sample, the sample liquid is emptied from the tip, the pipetting unit with pipette tip is raised, arm 1 moves to the waste container, the used tip is discharged, arm 1 moves into the starting position. |
| 82 | Arm 2 with the cap moves to the measuring cell or to the opening of the storage vessel |
| 83 | Operation sequence for capping and closing (arm 2) Arm 2 with the cap moves over the vessel opening, the cap is lowered onto the vessel, the cap is pulled off from the tapered withdrawal plug of the opening device, the vessel is closed with the cap arm 2 moves into the "stand-by" position. |

End of the sequence

The amplification mixture is now ready for the direct detection of the amplificates that are formed or for carrying out further reactions.

EXAMPLE 2

The following explains, with respect to FIGS. 8–11, how a cap handler can remove or attach a cap.

(A) OPENING THE CAP

The cap handler must be in the detent position A of the removal unit.

1) Place counter support 2003 (outer envelope) on the tube.

2) Upon a downward force, wiper envelope 2006 is depressed onto the cap while simultaneously stop spring 2004 is stressed. Thereupon a first pressure point is reached.

3) Upon applying a force larger than in step 2),
 a) the tapered removal plug 700 is displaced into the removal plug seat,
 b) the spring 2007 is compressed,
 c) the removal unit 2005 shortens the distance II and moves into the detent position B, the spring 2007 remaining in the stressed position.

A second pressure point is reached.

4) Releasing the cap handler (eliminating the downward force) causes the cap to be removed from the tube. The force required to overcome friction is provided by releasing the stress on stop spring 2004. The force is transmitted through the element 2003 and the tapered removal plug 700 onto the cap and the tube ribs.

5) The cap handler together with the cap now can be lifted and removed.

Because of the shortened distance II, tapered removal plug 700 is now retracted into the casing 2002.

Presently the cap is partially protected against contamination by counter support 2003 while operatively projecting 1–2 mm beyond counter support 2003.

(B) CLOSING THE CAP

6) The cap handler together with the cap are set on the tube aperture and by applying a downward force the cap is moved into the tube aperture 7) Increasing the force of 6) implements full insertion of the cap and its clamping in place by friction. The force is transmitted through the elements 2005, 2009, 2008, 2010 into tapered removal plug 700.

The spring 2004 is stressed simultaneously.

A third pressure point is reached.

8) By increasing the force in step 7), the tapered removal plug 700 is moved out of wiper envelope 2006. At the same time the spring 2004 is stressed further and removal unit 2005 moves back into the initial detent position A and lengthens the distance II.

9) By reducing or releasing the downward force, the cap handler is moved fully upward, the stressed spring 2004 acting through counter support 2003 depressing the tube. The spring is released in this procedure and the cap handler is ready for another opening procedure.

Legend
1 reaction vessel
101 inner wall of the reaction vessel
102 barb
2 holding plate
3 holes in the holding plate
4 thermoblock
5 cap
500 part of the reaction vessel that protrudes from the reaction vessel
501 stop
503 surface of the cap
550 part that protrudes into the opening of the reaction vessel
551 means for removing the cap
552 sealing ring
553 intervening space
554 external surface of the cap directed towards the inner wall 101
555 septum
7 opening device/removal device
700 tapered removal plug
701 removal ring
710 stripping jacket
2100 removal device
2101 pressure piece 2102 stop jacket
2103 stop element
2105 pressure pin
2106 pressure spring
2001 mounting
2002 casing
2003 counter support
2004 stop spring
2005 cross-slotted screw
2006 wiper envelope
2007 spring
2008 thrust element
2009 thrust element
2010 thrust element
010 composite plate with reaction vessels and caps
011, 012, 013 reagent storage vessels
014, 015, 016 sample vessels
017 pipetting unit
018 gear rack
8 screw cap
801 screw thread
802 opening of the screw cap for sampling
9 pipet

We claim:

1. A system for automatically carrying out reactions in liquid sample analysis, said system comprising:
   a plurality of reagent storage vessels for storing reagent therein;
   a plurality of sample storage vessels for storing liquid sample therein;
   a plurality of reaction vessels;
   wherein at least one plurality of vessels selected from said plurality of reagent storage vessels, sample storage vessels, and reaction vessels include individual closures, said individual closures being disposed to be removed from and replaced upon a corresponding one of the at least one plurality of vessels; said system further comprising
   automatic opening means for automatically opening the individual closures of the at least one plurality of vessels by automatically removing the individual closures, and for closing the at least one plurality of vessels by placing the individual closures thereupon, said automatic opening means comprising
   an outer housing;
   a linear movement means coaxially disposed within said outer housing, and configured to linearly and coaxially move within said outer housing, wherein an engagement means is disposed at a distal end of said linear movement means, said engagement means for engaging and removing one of said individual closures; and disengagement means for disengaging a removed individual closure from said engagement means, said disengagement means being disposed adjacent said engagement means.

2. A system as recited in claim 1, further comprising a vessel support means for supporting said plurality of reaction vessels.

3. A system as recited in claim 1, further comprising automatic pipetting means for automatically pipetting liquid to and from at least one of said plurality of reagent storage vessels, sample storage vessels, and reaction vessels.

4. A system as recited in claim 1, further comprising temperature regulation means for regulating the temperature of liquid contained in the plurality of reaction vessels.

5. A system as recited in claim 2, wherein said vessel support means supports said plurality of reaction vessels, said plurality of sample storage vessels, and said plurality of reagent storage vessels.

6. A system as recited in claim 1, wherein said automatic opening means includes an engagement means for engaging one of said individual closures, and wherein said automatic opening means includes moving means for moving the engagement means to engage the one of the individual closures, to remove the one of the individual closures, and which includes disengagement means for disengaging the removed closure from the engagement means.

7. A system as recited in claim 1, further comprising selection means for selectively moving said automatic opening means to a selected one of said plurality of reagent storage vessels, sample storage vessels and reaction vessels.

8. A system for automatically carrying out reactions in liquid sample analysis, said system comprising:
   a plurality of reagent storage vessels for storing reagent therein;
   a plurality of sample storage vessels for storing liquid sample therein;
   a plurality of reaction vessels;
   wherein at least one plurality of vessels selected from said plurality of reagent storage vessels, sample storage vessels, and reaction vessels include individual closures, each of said individual closures comprising one cap having an extending part configured to extend into an open end of the vessel, said engagement surface comprising a circular sealing ring which engages the inner surface, said extending part including an engagement surface for engaging and sealing an inner surface of said vessel, said extending part including receiving means therein, and wherein the system includes removing means for engaging the receiving means and for removing the cap from the vessel, said removing means being received by the receiving means thereby being located within said open end of the vessel if the vessel is closed by the one cap.

9. A system cap as recited in claim 8 wherein, said cap further comprises a sealing ring disposed on said extending portion, said sealing ring for engaging said inner surface of said vessel.

10. A system as recited in claim 8, wherein a portion of said extending part of said cap, facing an inner portion of said vessel, includes a flat surface.

11. A system as recited in claim 8, wherein said cap is configured to fit within an aperture in a screw cap, and wherein said screw cap includes threaded portions to engage correspondingly threaded portions of the liquid storage vessel.

12. A system for automatically carrying out reactions in liquid sample analysis, said system comprising:
   a plurality of reagent storage vessels for storing reagent therein;
   a plurality of sample storage vessels for storing liquid sample therein;
   a plurality of reaction vessels;
   wherein at least one plurality of vessels selected from said plurality of reagent storage vessels, sample storage vessels, and reaction vessels include individual closures, each of said individual closures comprising one cap having an extending part configured to extend into an open end of the vessel, said extending part including an engagement surface for engaging and sealing an inner surface of said vessel, said extending part including receiving means therein, and wherein the system includes removing means for engaging the receiving means and for removing the cap from the vessel, said removing means being connected to automatic opening means for automatically opening and closing the individual closures of the at least one plurality of vessels by automatically removing or fixing the individual closures, wherein said cap further comprises a first cylindrical portion for extending into and engaging the inner surface of said vessel, and a second cylindrical portion, coaxially disposed within said first cylindrical portion, said second cylindrical portion being connected to said first cylindrical portion by a connecting portion, said second cylindrical portion for receiving said removing means therein.

13. A system for mechanically performing reactions in liquid sample analyses, said system comprising:

a plurality of reagent storage vessels for storing reagent therein;

a plurality of sample storage vessels for storing liquid sample therein;

a plurality of reaction vessels;

wherein at least one plurality of vessels selected from said plurality of reagent storage vessels, sample storage vessels, and reaction vessels include individual closures, said individual closures being disposed to be removed from and replaced upon a corresponding one of the at least one plurality of vessels, said system further comprising:

mechanical opening means for mechanically opening a selected one of the at least one plurality of vessels, said mechanical opening means including an engagement means for engaging a surface of one of the individual closures, said engagement means including a raised removal ring for engaging the surface of the one of the individual closures, and wherein the mechanical opening means includes moving means for moving the engagement means to remove and replace each of the individual closures on corresponding ones of the plurality of vessels, wherein said mechanical operating means is manually operated.

14. A system for mechanically performing reactions as recited in claim 13, wherein said at least one plurality of vessels is supported on a vessel support means.

15. Apparatus seizing a removable cap of a vessel, said apparatus comprising:

tapered removal means for projecting into an interior of the cap for clamping and securing said cap, and said tapered removal means including an engagement means for engaging and removing said cap, said engagement means including a raised removal ring for engaging and thereby clamping and securing the cap; and a stripping means for stripping the cap secured to the tapered removal means from said tapered removal means.

16. Apparatus seizing a removable cap of a vessel, said apparatus comprising a tapered removal means for projecting into an interior of the cap for clamping and securing said cap, and said tapered removal means including an engagement means for engaging and removing said cap, a stripping means for stripping the cap secured to the tapered removal means from said tapered removal means, wherein said apparatus further comprises moving means for linearly moving said tapered removal means relative to the cap and the vessel, said moving means linearly moving said tapered removal means in a first direction toward said cap wherein said engagement means engages and secures said cap, and for moving said tapered removal means in a second direction, opposite from said first direction, for removing said cap from said vessel.

* * * * *